US 7,729,772 B2

(12) United States Patent
Williams et al.

(10) Patent No.: US 7,729,772 B2
(45) Date of Patent: Jun. 1, 2010

(54) IMPLANTABLE NEUROMODULATION SYSTEM AND METHOD

(75) Inventors: Jeffrey M. Williams, Andover, MN (US); Hans van den Biggelaar, Haaren (NL)

(73) Assignee: Uroplasty, Inc., Minnetonka, MN (US)

( * ) Notice: Subject to any disclaimer, the term of this patent is extended or adjusted under 35 U.S.C. 154(b) by 935 days.

(21) Appl. No.: 10/905,501

(22) Filed: Jan. 7, 2005

(65) Prior Publication Data
US 2006/0155345 A1 Jul. 13, 2006

(51) Int. Cl.
*A61N 1/36* (2006.01)
(52) U.S. Cl. ...................................................... 607/41
(58) Field of Classification Search .................. 607/40, 607/46, 59–61, 41
See application file for complete search history.

(56) References Cited

U.S. PATENT DOCUMENTS

| | | | | |
|---|---|---|---|---|
| 3,405,715 A | * | 10/1968 | Hagfors | 607/118 |
| 3,628,538 A | | 12/1971 | Belfast et al. | 128/422 |
| 3,727,616 A | * | 4/1973 | Lenzkes | 607/59 |
| 3,788,329 A | * | 1/1974 | Friedman | 607/122 |
| 3,796,221 A | * | 3/1974 | Hagfors | 607/59 |
| 4,102,344 A | * | 7/1978 | Conway et al. | 607/17 |
| 4,585,005 A | * | 4/1986 | Lue et al. | 607/39 |
| 4,607,639 A | * | 8/1986 | Tanagho et al. | 607/40 |
| 4,612,934 A | * | 9/1986 | Borkan | 607/62 |
| 4,739,764 A | | 4/1988 | Lue et al. | 128/419 |
| 4,771,779 A | | 9/1988 | Tanagho et al. | |
| 5,094,242 A | | 3/1992 | Gleason et al. | 600/377 |
| 5,112,296 A | | 5/1992 | Beard et al. | 602/28 |
| 5,211,175 A | | 5/1993 | Gleason et al. | 600/548 |
| 5,562,717 A | | 10/1996 | Tippey et al. | 607/41 |
| 5,814,093 A | | 9/1998 | Stein | 607/49 |
| 6,055,456 A | | 4/2000 | Gerber | 607/117 |
| 6,061,596 A | * | 5/2000 | Richmond et al. | 607/41 |
| 6,493,588 B1 | | 12/2002 | Malaney et al. | 607/46 |
| 6,652,449 B1 | | 11/2003 | Gross et al. | 600/30 |
| 6,662,052 B1 | | 12/2003 | Sarwal et al. | 607/59 |
| 6,735,474 B1 | * | 5/2004 | Loeb et al. | 607/41 |
| 6,941,171 B2 | * | 9/2005 | Mann et al. | 607/39 |
| 2003/0144710 A1 | | 7/2003 | Haugland et al. | 607/48 |
| 2004/0111126 A1 | | 6/2004 | Tanagho et al. | 607/40 |

FOREIGN PATENT DOCUMENTS

| | | |
|---|---|---|
| GB | 2302283 A | 1/1997 |
| GB | 2330912 A | 5/1999 |
| GB | 2368017 A | 4/2002 |
| WO | WO 82/01656 | 5/1982 |
| WO | WO 99/19019 | 4/1999 |
| WO | WO 03/033068 A2 | 4/2003 |
| WO | WO 2004/078255 A1 | 9/2004 |

* cited by examiner

*Primary Examiner*—George R Evanisko
(74) *Attorney, Agent, or Firm*—Clise, Billion & Cyr, P.A.

(57) ABSTRACT

An implantable neuromodulation system and method of treating a patient through neuromodulation of a patient's body tissue. The neuromodulation system includes a portable transmitter and an implantable receiver. The implantable receiver includes one or more electrodes disposed on the distal end of one or more elongated, flexible insulated leads. The transmitter is programmable with a treatment protocol to cause the transmitter to generate a pulsed, alternating magnetic field in accordance with the treatment protocol. When the transmitter is placed in close proximity to the receiver, the alternating magnetic field pulses generated by the transmitter cause the receiver to operably generate stimulating pulses delivered via the electrode(s) to the targeted tissue of the patient.

13 Claims, 10 Drawing Sheets

IMPLANTABLE NEUROMODULATION SYSTEM AND METHOD

BACKGROUND OF THE INVENTION

1. Field of the Invention

The present invention relates generally to nerve stimulation or neuromodulation and more particularly to implantable nerve stimulation or neuromodulation systems and methods.

2. Description of the Related Art

Urinary incontinence is a symptom that can be caused by a wide variety of conditions. Some urinary incontinence conditions are temporary and may result from urinary tract or vaginal infections, constipation, or the effects of medicine, including such medicines as diuretics, antidepressants and other drugs causing anticholinergic effects, as well as sedatives, narcotics, analgesics, etc. which can cause muscle relaxation, sedation, delirium, and/or immobility. Other urinary incontinence conditions are longer-lasting, and may even be permanent. Such longer lasting incontinence conditions may be caused by obesity, pregnancy and vaginal child birth, pelvic surgeries such as hysterectomies, trauma resulting in damage to the nerves that control the bladder, stroke, and chronic diseases that cause nerve and bladder neuropathy such as multiple sclerosis, diabetes and Parkinson's disease.

Incontinence is classified by the symptoms or circumstances occurring at the time of the urine leakage. Stress incontinence is a term used to refer to loss of bladder control resulting from poor bladder support by the pelvic muscles or by weak or damaged sphincter muscles. This condition allows urine to leak when the abdomen is stressed or strained, such as during coughing, sneezing, laughing, bending over and even walking. Urge incontinence results when the bladder contracts unexpectedly causing urine leakage. An overactive bladder may result from infection that irritates the bladder lining, nerve damage, and other conditions. Mixed incontinence is often a combination of both stress incontinence and urge incontinence. Overflow incontinence occurs when the bladder is allowed to become so full that it simply overflows. This happens when bladder weakness or a blocked urethra prevents normal emptying of the bladder. An enlarged prostate can result in such blockage. For this reason, overflow incontinence is more common in men that in women. Bladder weakness can develop in both men and women, but it happens most often in people with diabetes, heavy alcohol users, and others with decreased nerve function.

Overactive bladder ("OAB") is a combination of symptoms including urgency (the strong need to urinate), frequency (repetitive need to void) and/or urge incontinence. OAB is highly correlated with age and, for women, childbirth. OAB causes embarrassment to patients and very often negatively affects their social and sex lives. In the past, accurate data on the prevalence of OAB was unavailable partly due to the unwillingness of patients to discuss their symptoms and the market's common belief that there were no treatments. Recent epidemiological studies, however, have provided data on the prevalence of OAB symptoms in the adult population grouped according to age and gender. According to these studies 19.6 million Americans experience OAB and the incidences of OAB are projected to climb to 24.2 million by 2015. Researchers overwhelmingly report that these estimates could grossly underestimate those affected as women commonly accept OAB, secondary to childbirth, as something "to live with." Further, it is known that those affected are hesitant to discuss their symptoms with doctors as they are embarrassed by their condition and have been discouraged by the lack of solutions. As a result, less conservative studies estimate that OAB currently affects 53 million Americans.

To understand the causes of ("OAB") and the ability to treat OAB through nerve stimulation or neuromodulation, it is necessary to have a proper understanding of the urinary system and its operation.

Urine comprises waste and water removed from the blood by the kidneys. Urine flows from the kidneys downward through a pair of tubes, the ureters, to the bladder. The bladder is a balloon-like container that stores urine. Urine leaves the body through another tube, the urethra, at the bottom of the bladder.

The act of urinating is controlled by muscles that comprise the outflow controls, called sphincters, located at the base of the bladder and in the wall of the urethra, referred to as the detrusor muscles. In a healthy or normal urinary system, the sphincter muscles are constantly in a state of active contraction, except during the voluntary act of evacuation. Thus, in the contracted state, the contracted sphincter muscles close-off the neck of the bladder and the urethra, much like a tie at the base of a balloon, to prevent the flow of urine from the bladder. During urination, the sphincter muscles are relaxed thereby causing the neck of the bladder and the urethra to open. At the same time, the detrusor muscle contracts to squeeze the bladder thereby forcing the urine to evacuate the bladder. When the bladder is empty and urination is completed, the detrusor muscle returns to its normal relaxed state and the sphincter muscles again return to their normally contracted state, to close-off the neck of the bladder and urethra to prevent any further passage of urine from the bladder.

It is well known that electrical stimulation of the S2 and S3 sacral nerves can modulate the neuromuscular control of bladder function in a human. The S2 sacral nerve constitutes the main motor supply to the external sphincter muscle. Whereas the S3 sacral nerve constitutes the main motor supply to the detrusor muscle. It is also known that electrical stimulation of the tibial nerve at approximately two inches (5 cm) cephalic to the medial tibial malleolus, can stimulate the S2 and S3 sacral nerves, thereby enabling modulation of the bladder, in substantially the same way as if directly stimulating the S2 and S3 sacral nerves. Thus, modulation of the tibial nerve provides a less invasive and less costly method of achieving the same, if not better results, than the highly invasive spinal, abdominal or genito-pelvic implants which are more difficult to place, present a greater likelihood of complications, and necessarily involve higher costs.

Accordingly, there is a need for a nerve stimulation or neuromodulation system that is less invasive when compared to other neurostimulation implant procedures so as to minimize risk of complications and which is easier and less time consuming for the physician to place in the patient, but which is effective for both nerve and muscle stimulation for treatment of numerous conditions, including, but not limited to, urge incontinence, urinary frequency, non-obstructive urinary retention and interstitial cystitis, as well as for treating chronic pain, Parkinson's disease, multiple sclerosis and other neuromuscular disorders and for general muscle and joint rehabilitation.

SUMMARY OF THE INVENTION

An implantable neuromodulation system and method of treating a patient through neuromodulation of a patient's body tissue. The neuromodulation system includes a portable transmitter and an implantable receiver. The implantable receiver includes one or more electrodes disposed on the distal end of one or more elongated, flexible insulated leads.

The transmitter is programmable with a treatment protocol to cause the transmitter to generate a pulsed, alternating magnetic field in accordance with the treatment protocol. When the transmitter is placed in close proximity to the receiver, the alternating magnetic field pulses generated by the transmitter cause the receiver to operably generate stimulating pulses delivered via the electrode(s) to the targeted tissue of the patient.

In the preferred method, two electrodes (one comprising the cathode, the other comprising the anode) are disposed in close proximity to the patient's tissue desired to be stimulated such that the stimulating pulses flowing from the cathode pass through the patient's tissue and flow into the anode. The duration and pulse characteristics of the treatment protocol are preferably selectively adjustable by a patient within predetermined ranges predefined by a physician or other health care provider.

DETAILED DESCRIPTION OF THE INVENTION

Figure 1:
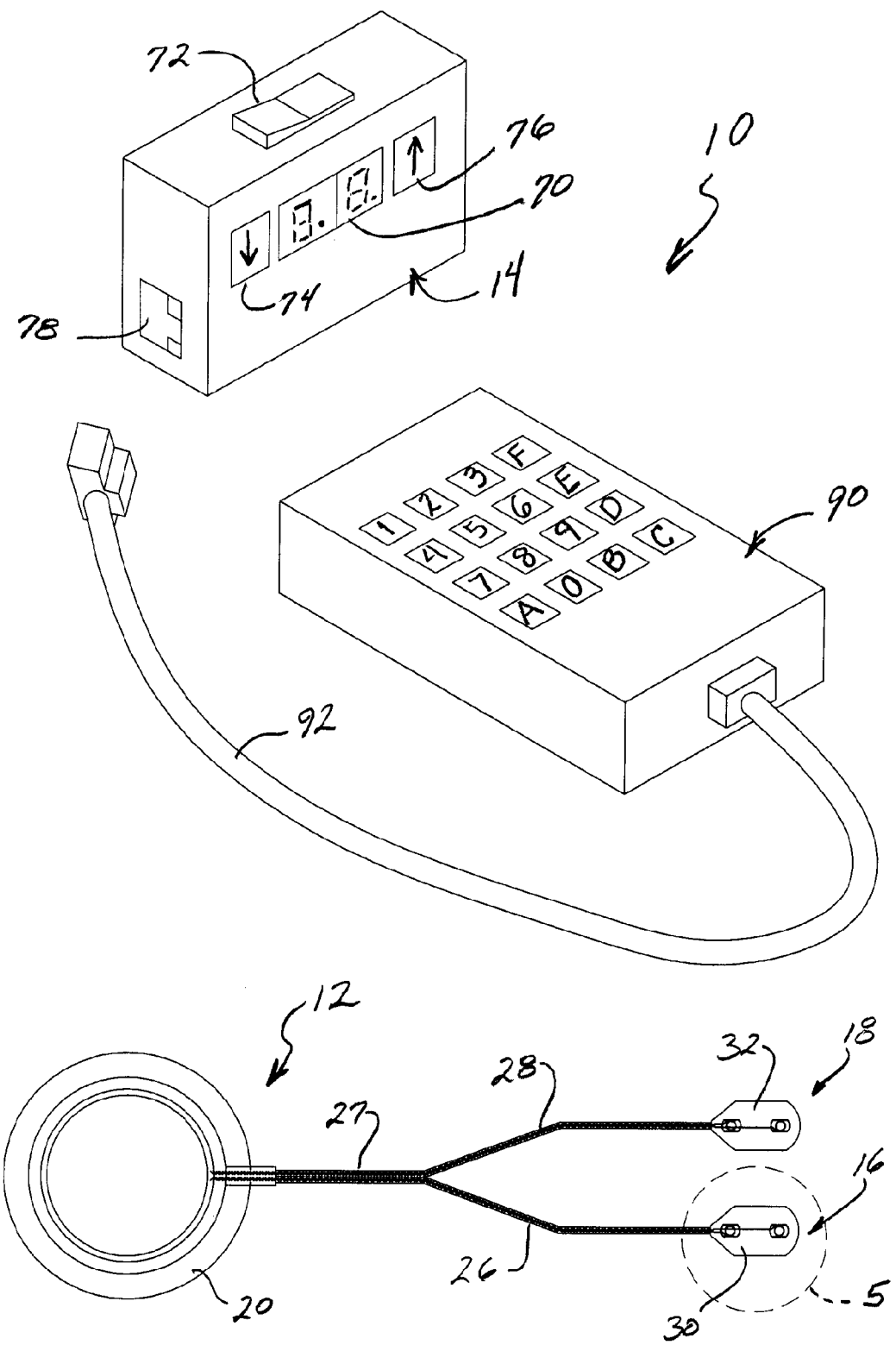
FIG. 1 illustrates one embodiment of the transmitter and receiver of the neuromodulation system of the present invention.
Figure 14:
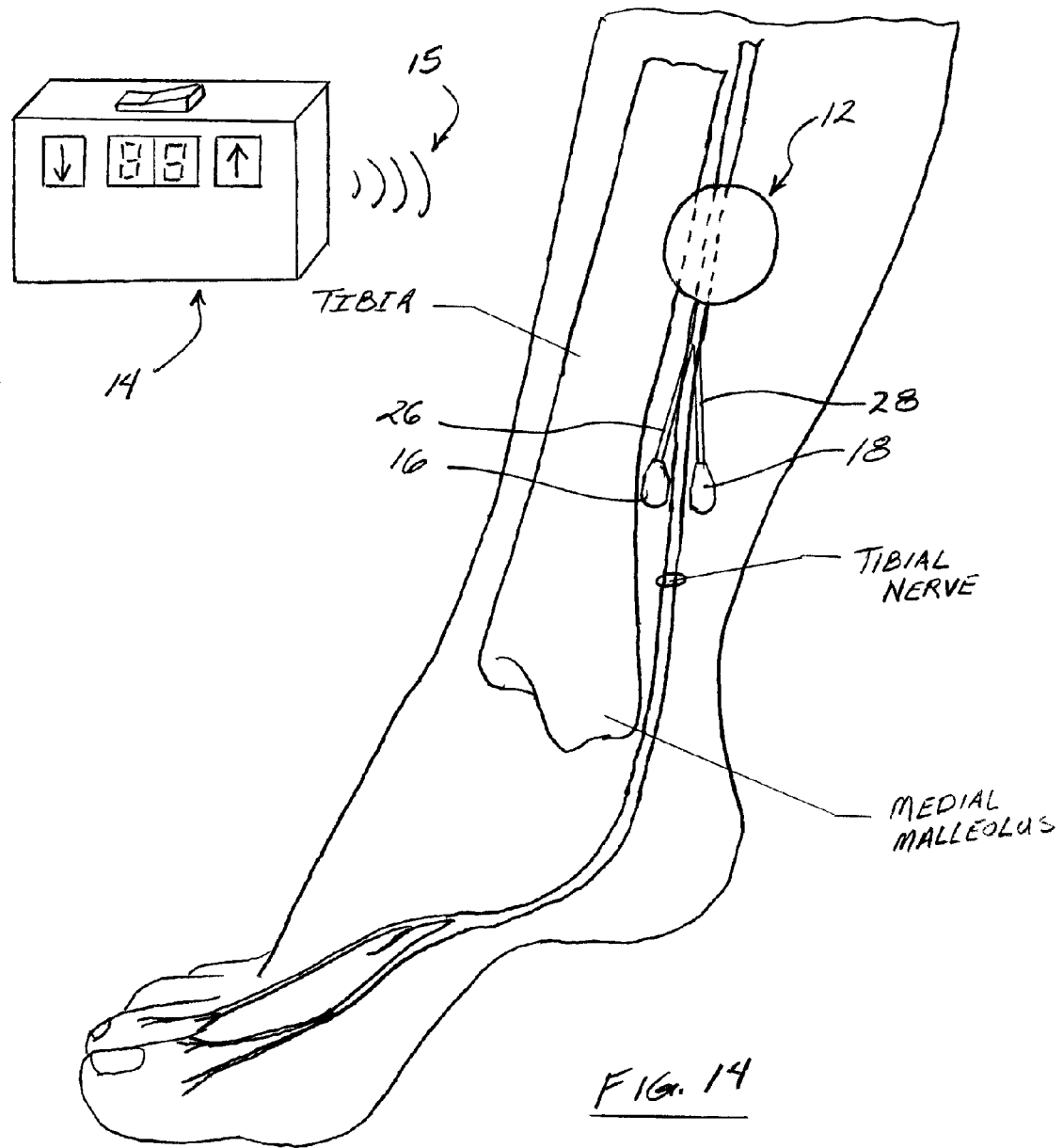
FIG. 14 illustrates placement of the receiver of FIG. 1 in relation to the tibial nerve of a patient in accordance with one method of use of the neuromodulation system of the present invention.

Referring to the drawings, wherein like reference numerals designate identical or corresponding parts throughout the several views, FIG. 1 illustrates one embodiment of the neuromodulation system 10 which comprises an implantable receiver 12, and a portable transmitter 14. The transmitter 14 is preferably battery powered and sized to be easily transportable. In operation, as described in greater detail later, the transmitter 14 generates a pulsed, alternating magnetic field as indicated by reference numeral 15 (FIG. 14). When the transmitter 14 is placed in close proximity to the implanted receiver 12, the alternating magnetic field pulses 15 generated by the transmitter 14 cause the implanted receiver 12 to operably generate stimulating pulses delivered via one or more electrodes to the targeted tissue of the patient. In the preferred embodiment, the receiver 12 preferably includes two separate electrodes 16, 18, one acting as the cathode, the other acting as the anode. It should be appreciated, however, that the implantable receiver 12 may utilize only one electrode to deliver the stimulating pulses to the patient's tissue.

Figure 2:
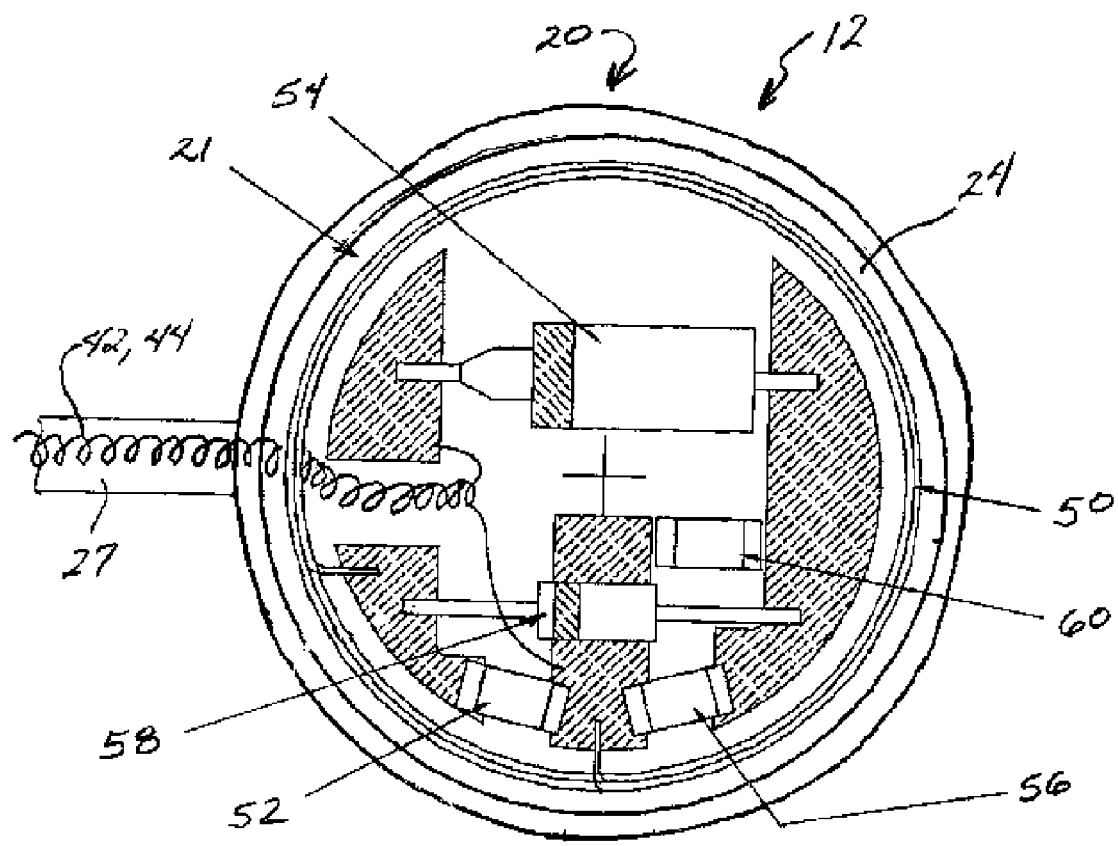
FIG. 2 is a detailed plan view of one embodiment of the receiver head of FIG. 1.
Figure 3:
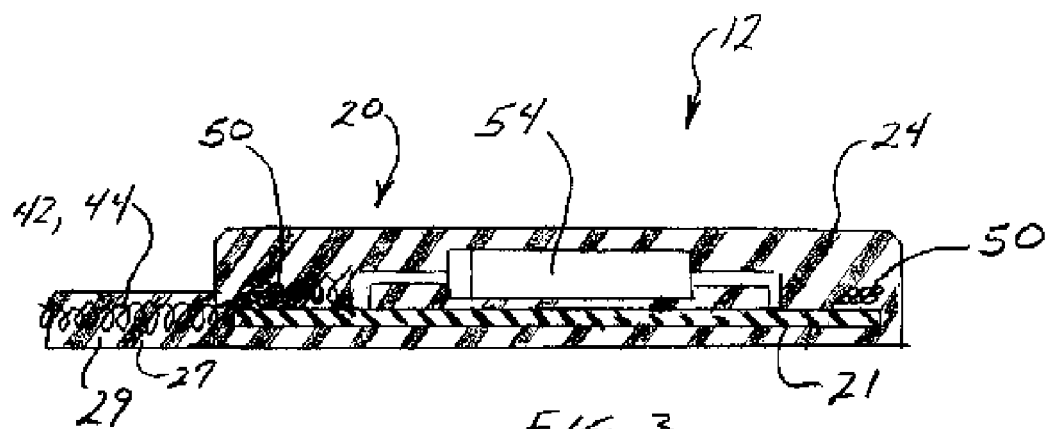
FIG. 3 illustrates a cross-sectional view of the receiver head of FIG. 2 as viewed along lines 3-3 of FIG. 2.
Figure 4:
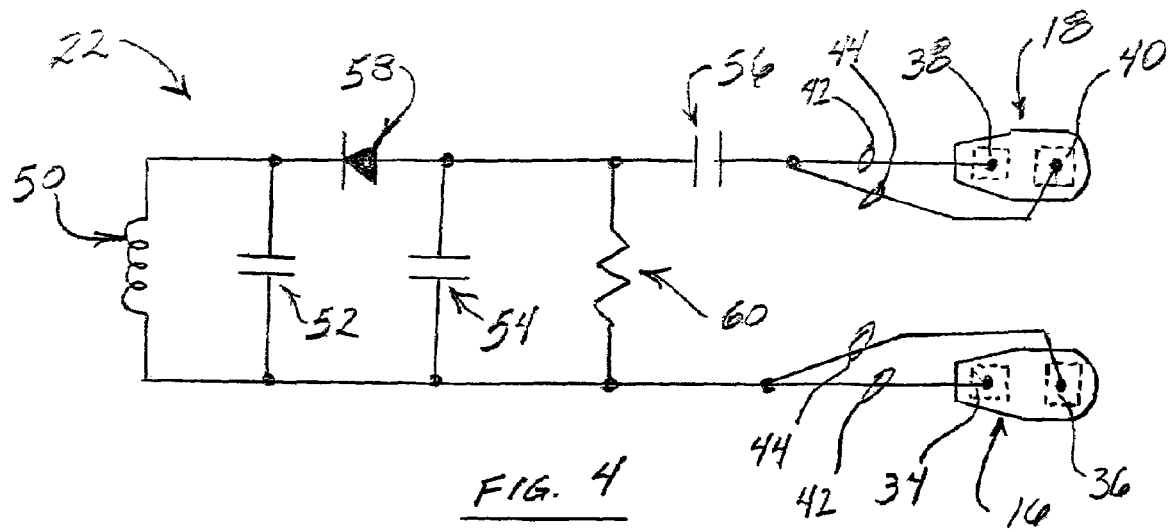
FIG. 4 is a schematic of one embodiment of an electrical circuit for the receiver of FIG. 1.

In the embodiment illustrated in FIGS. 2 and 4, the receiver 12 comprises a head 20 containing the receiver circuitry 22. The head 20 includes a circuit base disk 21 (FIG. 3) upon which the various components comprising the circuitry 22 are affixed. The circuit base disk 21 and circuit components are preferably encapsulated within a shell 24 of dielectric, bio-compatible material, such as silicon, polyurethane, or the like, to seal the components and to prevent current leakage from the head 20. In the preferred embodiment of the receiver 12 the two electrodes 16, 18 are electrically connected to the circuitry 22 in the head 20 by two leads 26, 28 (FIG. 1) which preferably branch from a single lead stem 27. In the preferred embodiment, the branching leads 26, 28 are approximately ten centimeters long and comprise two electrically conductive wires 42, 44 encapsulated within a dielectric, resilient, bio-compatible sheath or casing 29 which insulates and seals the electrically conductive wires 42, 44 to prevent current leakage along their length.

Figure 5:
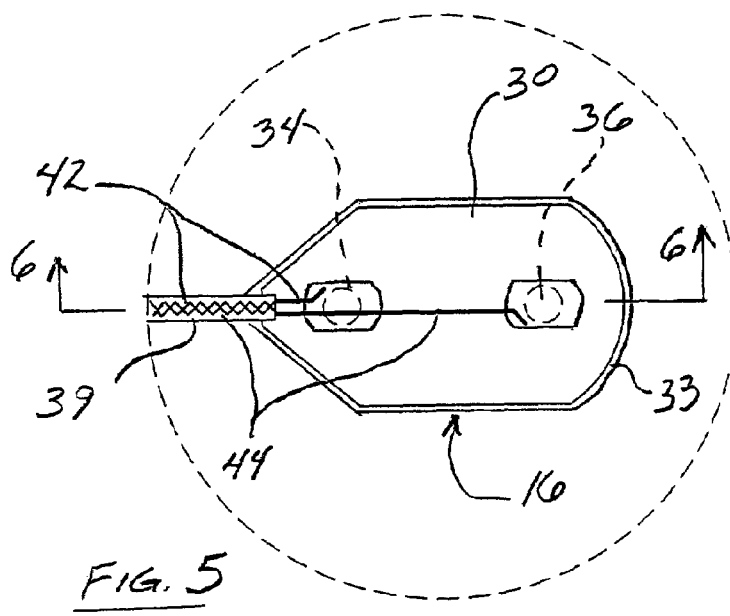
FIG. 5 illustrates one embodiment of an electrode of the receiver of FIG. 1.

As best illustrated in FIGS. 1 and 5, in the preferred embodiment, electrically conductive enlarged bases 30, 32 are disposed on the distal ends of the leads 26, 28. These enlarged bases 30, 32 are also preferably substantially encapsulated within a shell 33 of dielectric, bio-compatible material, except for one or more spaced apart raised areas or buttons 34, 36 and 38, 40 that are exposed or not insulated. The bases 30, 32 and exposed buttons 34, 36 and 38, 40 are preferably platinum, gold or other bio-compatible, highly electrically conductive material. The dielectric shell 33 surrounding the bases 30, 32 prevents current leakage about the surface area of the bases 30, 32 except at the exposed buttons 34, 36 and 38, 40, such that the stimulating current pulses are concentrated at the exposed buttons 34, 36 and 38, 40. In the preferred embodiment, the two buttons on each base 30, 32 carries the same electrical polarity, such that one lead 26 has two anodes 34, 36 and the other lead 28 has two cathodes 38, 40. By providing two anodes 34, 36 and two cathodes 38, 40 per base, each electrode 16, 18 offers a larger contact surface and thus allows for a larger field of charge. Additionally, it is recognized that high current density may lead to burns of the human tissue and/or degradation of the electrode surface. Thus, it is preferable to have a larger surface area by which to deliver the current pulses. It should be appreciated, however, that if the receiver 12 includes only a single electrode, the single electrode lead may terminate at its distal end with a single enlarged base having both an anode button and a cathode button.

Figure 6:
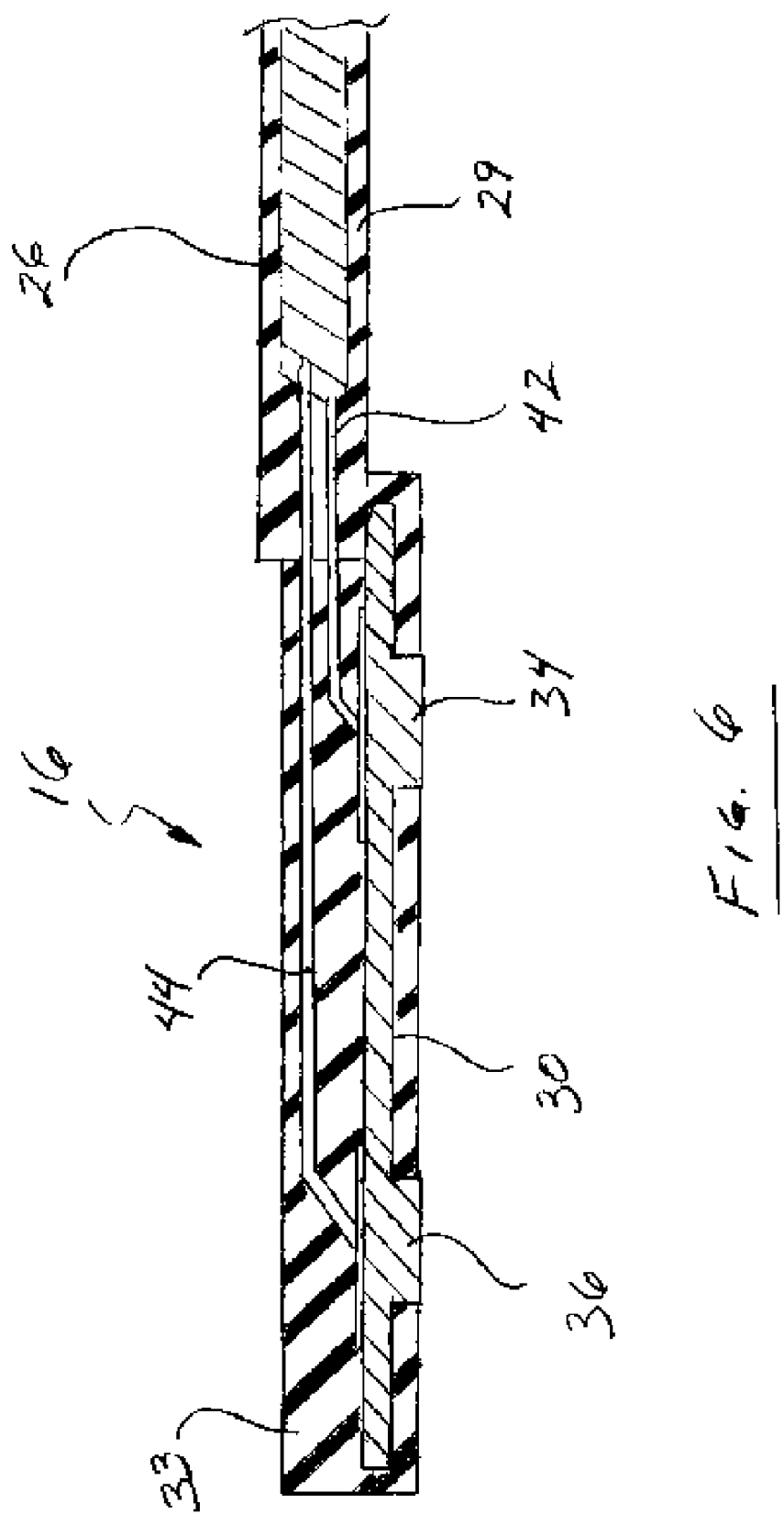
FIG. 6 illustrates a cross sectional view of the electrode of FIG. 5 as viewed along lines 6-6 of FIG. 5.

As previously discussed and as best illustrated in FIGS. 4, 5 and 6, each lead 26, 28 preferably includes electrically conductive wires 42, 44. Each of the wires 42, 44 in each lead 26, 28 is preferably coiled or helical. The helical wires 42, 44 in combination with the resilient dielectric sheath 29, allows the leads to elongate and provides flexibility and resiliency for ease of manipulation and placement at a desired stimulation site during the implanting procedure. Particularly, the resiliency of the leads enables the physician to place the electrodes at the desired stimulation site with a simple loop suture about the leads or bases without the need for clamping, sizing or performing any other modifications during surgery. Additionally, the length, flexibility and resiliency of the leads enables the receiver head 20 to be placed in a more easily accessible location. It is desirable to provide two separate wires 42, 44 in each lead 26, 28, each connected to the electrically conductive bases 30, 32, in order to provide redundancy in the event one of the wires breaks or is damaged during the implant procedure or while in use by the patient. The redundant wires will allow each pair of anodes 34, 36 and cathodes 38, 40 of the respective electrodes 16, 18 to continue to function even if one wire is damaged, thereby reducing the likelihood of having to remove and replace the implanted receiver 12. It should be appreciated, however, that if the receiver 12 includes only a single electrode, the single electrode lead would also preferably include two helical wires, one connecting to the anode button and one connecting to the cathode button on the single enlarged base.

In use, as described in greater detail later, with two electrodes 16, 18, each electrode is placed in close proximity to the nerve, muscle or other body tissue desired to be stimulated such that the stimulating pulses pass or flow in one direction from the cathode 18 into the target tissue before being received by the anode 16. In embodiments utilizing a single electrode, the stimulated pulses would pass from the cathode button into the tissue and back substantially along the same path before being received by the anode.

Referring now to FIG. 4 in combination with FIG. 2, one embodiment of the receiver circuitry 22 is illustrated. In this embodiment, the receiver circuitry 22 includes an inductive coil 50 and first, second and third capacitors 52, 54, 56, a diode 58, and resister 60. When the transmitter 14 is placed in close proximity to the implanted receiver head 20, the alternating magnetic field pulses 15 generated by the transmitter 14 induce current pulses in the inductive coil 50 with alternating polarity between the ends of the coil wire. In this embodiment, the inductive coil 50 is approximately 18.5 mm in diameter and includes nineteen turns using 0.15 mm enamel coated copper wire. The first capacitor 52 tunes the coil 50 to the high-frequency magnetic pulses emitting from the transmitter 14 such that the coil 50 is more sensitive to frequencies near the circuit's resonant frequency and less sensitive to frequencies away from the resonant frequency. In this embodiment, the tuning capacitor 52 is a 470 pF ceramic chip, nickel barrier, NPO dielectric, 1206 size. The diode 58 allows the current that is produced by the coil 50 to pass in one direction only. The diode 58 may be an IN914 diode or any other suitable diode. The second capacitor 54 and resistor 60 filter out the high frequency component of the receiver signal, thereby producing a current pulse of the same duration as the pulses of the high frequency magnetic field 15 emitted by the transmitter 14. In this embodiment, the second capacitor 54 is a 22 nF capacitor. The third capacitor 56 preferably blocks any net direct current so that the net charge transferred to the tissue is zero, in that, when the current pulse is completed and the voltage across capacitor 54 and resistor 60 becomes zero, the capacitor 56 discharges and thus causes the current in the tissue to reverse. This current reversal during the interval between stimulus pulses reverses the charge that was formerly built-up in the tissue and the capacitor 54 as current passed through the tissue during stimulus pulses. The third capacitor 56 is 1 µF 50V and may be a solid tantalum hermetic TAA series capacitor or SMD model. Preferably, during treatment, the receiver 12 generates a current pulse not in excess of 10 mA.

Referring again to FIG. 1, the transmitter 14 preferably includes a display 70 (such as an LED, LCD or other suitable display), an on/off power switch 72, and preferably two push-button controls 74, 76 for selectively controlling the treatment protocol, including the treatment duration, and pulse signal characteristics as hereinafter described.

Figure 7:
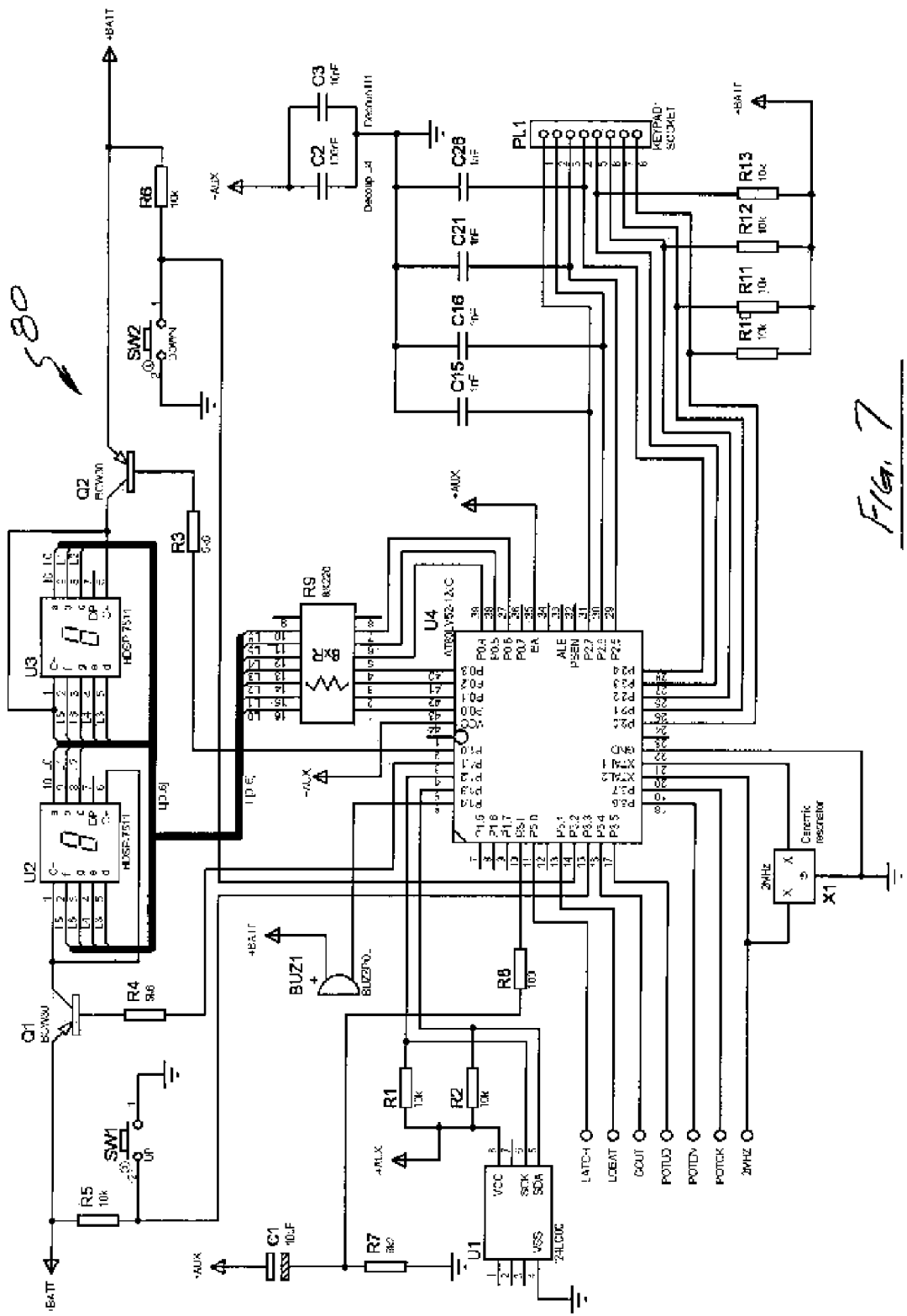
FIG. 7 is a schematic of one embodiment of a microcontroller circuit for the transmitter of FIG. 1.
Figure 8:
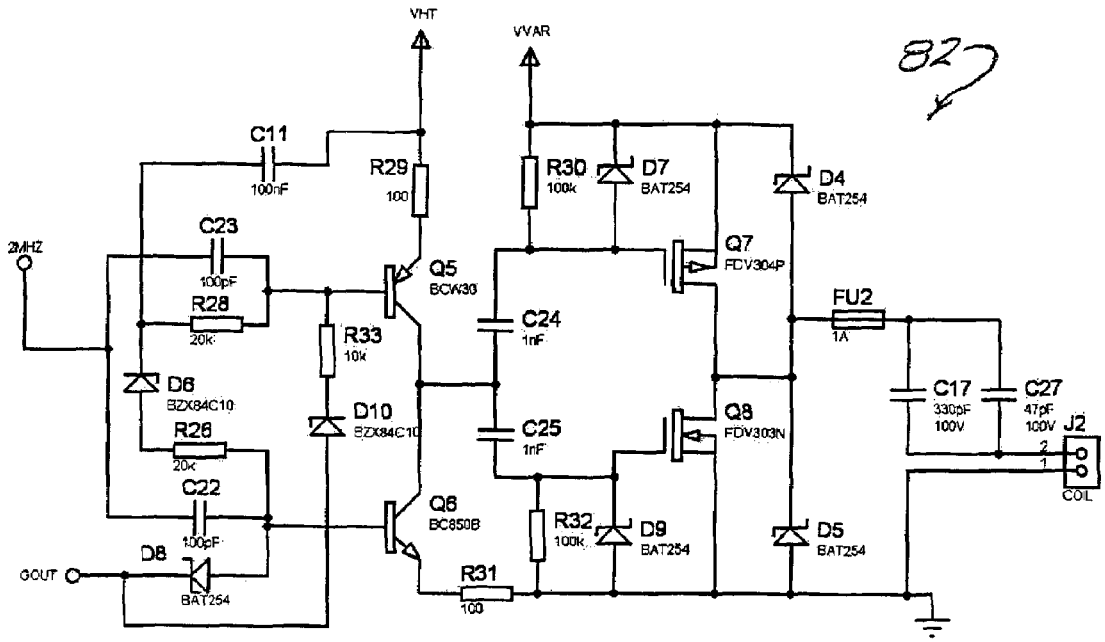
FIG. 8 is a schematic of one embodiment of a driver circuit for the transmitter of FIG. 1.
Figure 9:
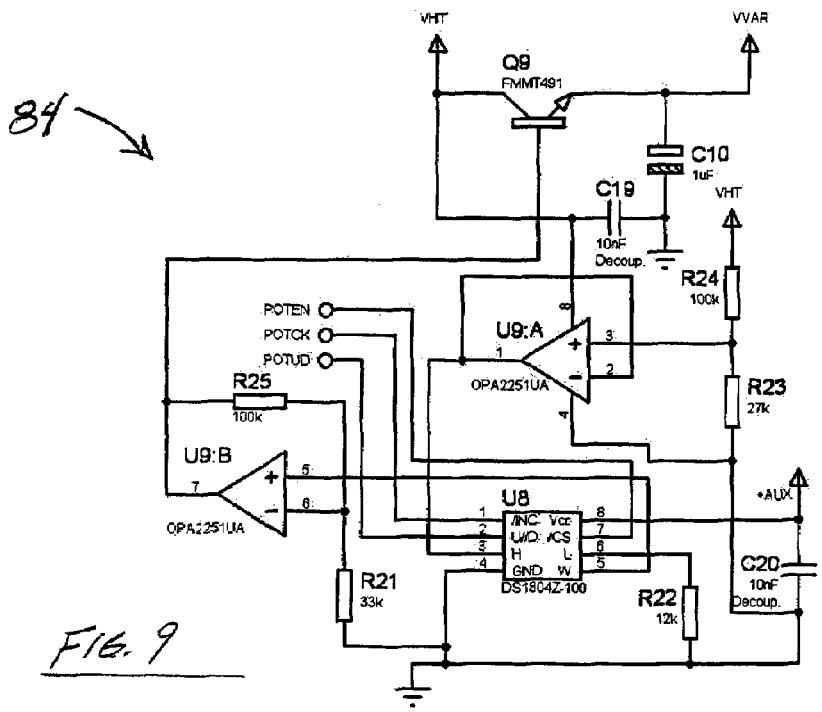
FIG. 9 is a schematic of one embodiment of an amplitude adjustment circuit for the transmitter of FIG. 1.
Figure 10:
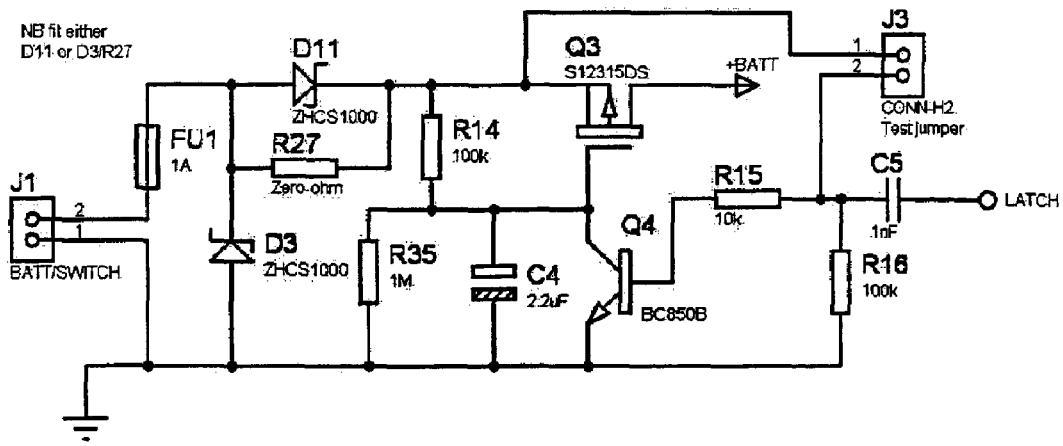
FIG. 10 is a schematic of one embodiment of a voltage regulator circuit for the transmitter of FIG. 1.
Figure 11:
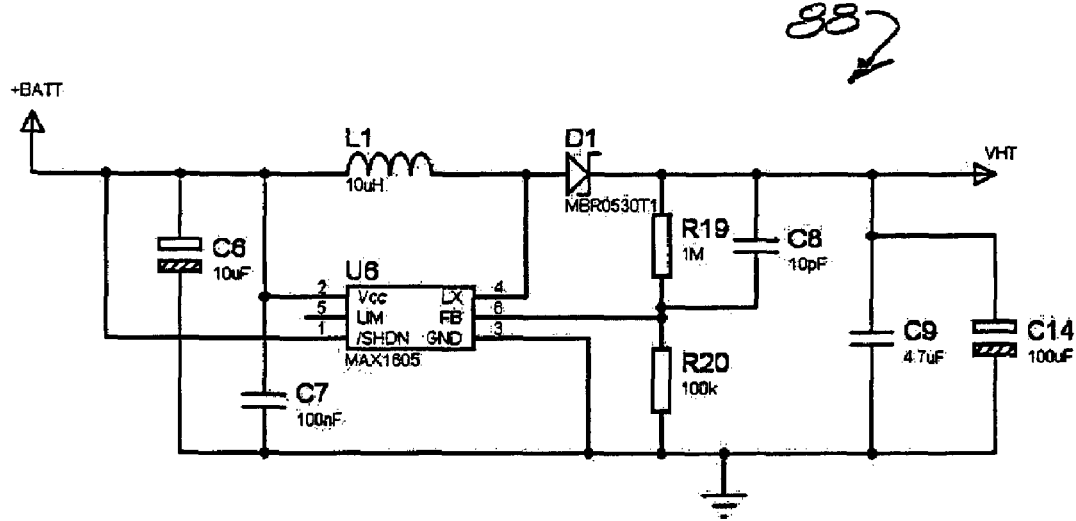
FIG. 11 is a schematic of one embodiment of a step-up voltage circuit for the transmitter of FIG. 1.

One embodiment of the transmitter circuitry 80 is illustrated in FIGS. 7 and 8. In this embodiment, the transmitter circuitry 80 includes a programmable microprocessor U4 which is coupled to a driver circuit 82 (FIG. 8) and switches SW1 and SW2 (FIG. 7) corresponding to the push-button controls 74, 76, which allows the patient to selectively adjust the treatment protocol, e.g., the frequency, duration, and/or the amplitude and/or width of the alternating magnetic field pulse that is output through the coil J2 (FIG. 8) of the driver circuit 82. The microprocessor U4 is coupled to display modules U2, U3 (FIG. 7) comprising the display 70 (FIG. 1) for displaying the readout of the transmitter settings controlled by switches SW1 and SW2. To enable selective adjustment of the pulse amplitude via switches SW1 and/or SW2, the transmitter circuitry 80 may include circuitry, such as illustrated in FIG. 9 designated generally by reference numeral 84. As illustrated in FIG. 10 the transmitter circuitry 80 may include voltage regulating circuitry, designated generally by reference numeral 86, for regulating the voltage via switches SW1 and SW2 and the microprocessor U4. As identified in FIG. 11, the transmitter circuitry 80 may also include step-up voltage circuitry, designated generally by reference numeral 88, for stepping up the voltage from the illustrated 9 volt DC battery power source for generating the alternating magnetic field pulses 15. Preferably, the alternating magnetic field pulses produced by the transmitter circuitry 80 is such that the current pulse delivered by the electrodes 16, 18 to the patient's tissue does not exceed 10 mA (based on a 1000 ohm load).

Those skilled in the art will recognize that the features and functionalities of the transmitter circuitry 80 and receiver circuitry 22 as described above may be accomplished through a variety of different circuit types and electrical components. Therefore, the present invention should not be construed as being limited to the specific circuitry and electrical components identified above.

In order to enable the transmitter 14 to be kept to a compact size for portability, the transmitter 14 may include a port 78 (FIG. 1) (corresponding to port PL1 in FIG. 8), for interfacing with a sixteen-key alpha-numeric keypad 90 (FIG. 1) via cable 92 for programming the microprocessor U4 of the transmitter 14 with a desired treatment protocol suitable the patient's condition being treated. Once the treatment protocol is programmed into the transmitter 14 via the keypad 90, the keypad 90 may be disconnected. Those of skill in the art will appreciate that other wired or wireless means of interfacing with and programming the microprocessor may also be suitable, including, but not limited to, for example, infra red (IR) communication using dedicated communication protocols. Preferably, the keypad 90 or interfacing means is only available to the physician or health care provider who programs the transmitter 14 with the treatment protocol suitable for treating the patient's condition.

Through the up and down arrow pushbuttons 74, 76 as illustrated in the drawing figures, depending on the treatment protocol programmed by the treating physician, the patient may have the ability to selectively adjust the treatment protocol and/or pulse characteristics, such as the pulse amplitude, pulse width, duty cycle (i.e., treatment duration and pulse frequency), etc., within a predetermined limited range or window defined by the treating health care provider. For example, the keypad 90 may be utilized to program the transmitter 14 with a treatment protocol within which the patient, through the pushbuttons 74, 76, is able to select between a default pulse frequency of, for example, 12 Hz and an alternate frequency of 20 Hz. Additionally, the keypad 90 may be used to program the transmitter with a treatment protocol with a default duration of thirty minutes, but through the push buttons, the patient may adjust the default treatment duration for example, by one minute increments between one and sixty minutes per treatment. Additionally, the keypad 90 may be used to program the transmitter 14 with a treatment protocol whereby the default pulse width is, for example 200 μs, and/or whereby the default pulse amplitude is, for example, 10 mA. The pushbuttons 74, 76 may be used to adjust the pulse width and/or pulse amplitude in predetermined increments. To ensure that the patient does not adjust the treatment protocol too greatly from the physician's recommended treatment protocol, it is preferred that the patient's adjustment options are limited. For example, the physician preferably defines the modulation type as being either the pulse width adjustable or amplitude adjustable, not both, such that only one of these variables is adjustable while the other remains fixed. Similarly, it is generally preferable that the pulse frequency is preset and fixed by the physician, so that the patient is only able to adjust the duration of the pulses, not the frequency and duration.

The transmitter is preferably programmed to stop treatment therapy after a preset time period and preferably includes safety features whereby treatment cannot be reinitiated within a defined time period so as to prevent over treatment or excessive stimulation by the patient. Furthermore, the transmitter also preferably includes means for recording a patient's use of the system which can be communicated by any suitable means, such as by downloading, printing, etc., for viewing by the treating physician or caregiver to enable the physician or caregiver to monitor the patient's use of the system.

Figure 12:
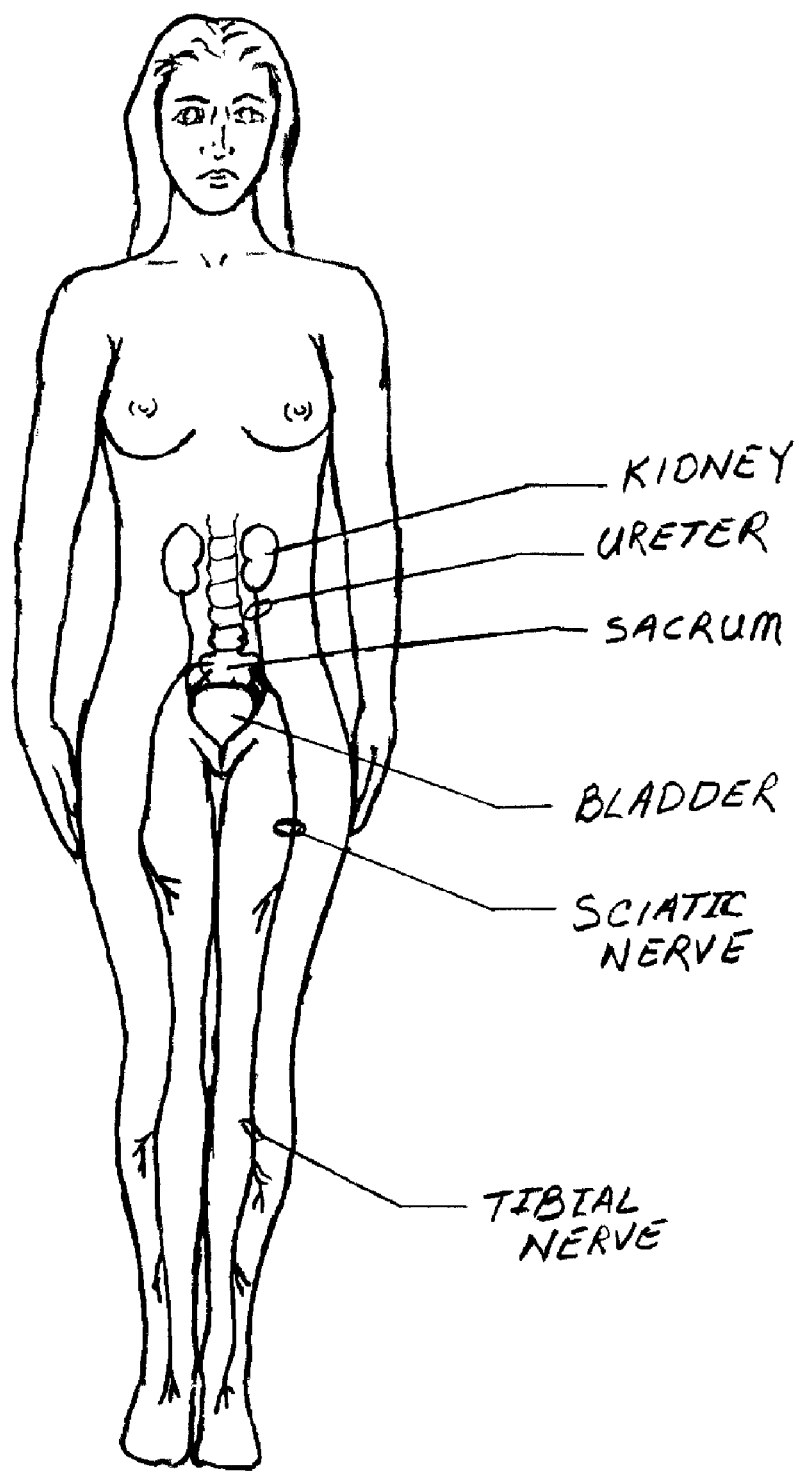
FIG. 12 is a general illustration of a patient's urinary system and sciatic and tibial nerves.
Figure 13:
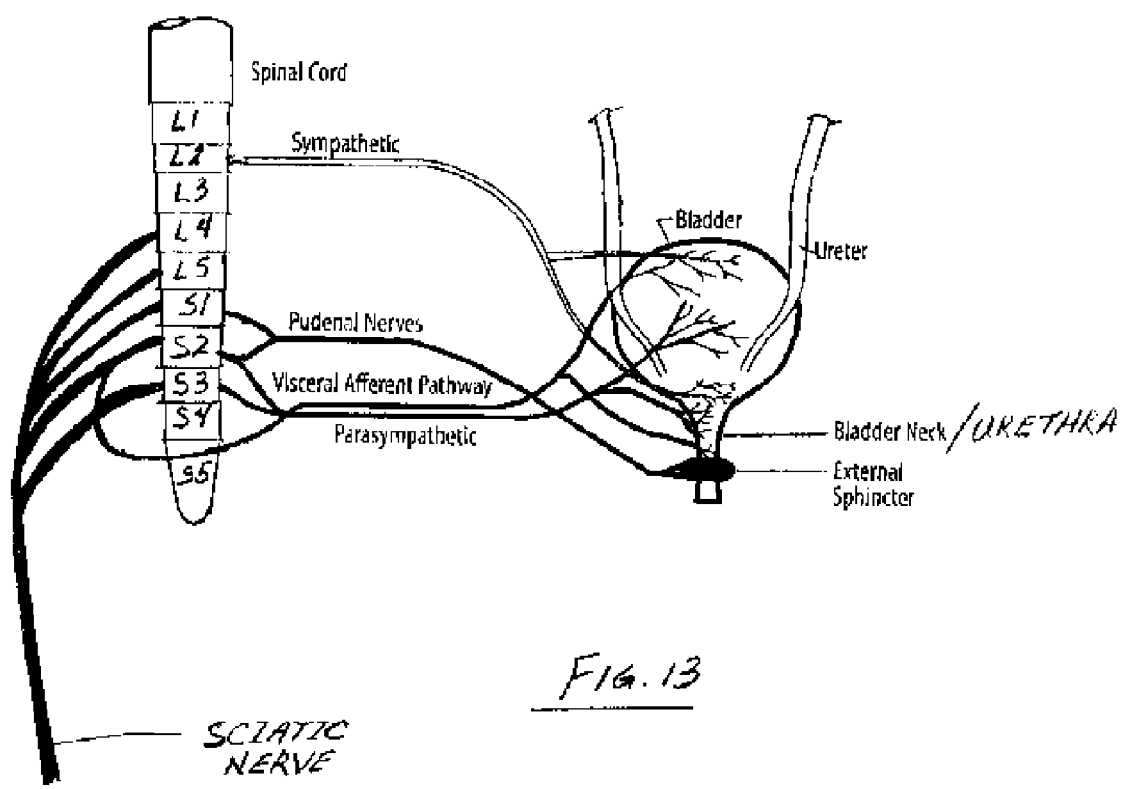
FIG. 13 is a more detailed illustration of the urinary system illustrated in FIG. 12 in relation to the sacral nerves.

The neuromodulation system 10 of the present invention is particularly adapted for treating urinary incontinence in a patient. As previously identified, it is well known that electrical stimulation of the S2 and S3 sacral nerves as illustrated in FIGS. 12 and 13 can modulate bladder function in a human. The S2 sacral nerve constitutes the main motor supply to the external sphincter muscle. Whereas the S3 sacral nerve constitutes the main motor to the bladder. It is also known that electrical stimulation of the tibial nerve at approximately five centimeters cephalic to the medial tibial malleolus (FIG. 14), can stimulate the S2 and S3 sacral nerves, thereby enabling modulation of the bladder, in substantially the same way as if directly stimulating the S2 and S3 sacral nerves.

Accordingly, in one application of the neuromodulation system 10 of the present invention for treating urinary incontinence, as illustrated in FIG. 14, the head 20 of the receiver 12 is implanted in the patient's leg in a relatively easily accessible area, but, at the same time, in close enough proximity to the medial tibial malleolus such that the electrodes 16, 18 at the distal ends of the leads 26, 28 can be placed at approximately five centimeters cephalic to the medial tibial malleolus.

In another application of the neuromodulation system 10 of the present invention, also for treating urinary incontinence, rather than placing the receiver 12 to stimulate the sacral nerves, the receiver may be placed to stimulate the pudendal nerve, wherein the receiver 12 is implanted through an incision in the gluteus muscle to access the nerve in the pudendal canal also called Alcock's canal. Neuromodulation or stimulation of still other nerve pathways, such as the peroneal and sciatic nerves may also be use for treating urinary incontinence. In addition, those of ordinary skill in the art will recognize that the apparatus of the present invention may be used for treating other neuromuscular disorders or conditions by implanting the receiver at various other locations to stimulate particular nerve pathways or tissue using various treatment protocols.

The surgical procedure for the application in which the receiver is implanted to stimulate the tibial nerve includes the following steps: Generally, the patient is first anesthetized, either totally or locally by a spinal injection, or possibly even with a local anesthetic. A small incision is then made in the skin in the area where the receiver is to be implanted. As illustrated in FIG. 14, in the method of treating urinary incontinence through neuromodulation of the tibial nerve, an incision of about five centimeters is made between approximately five and ten centimeters cephalic of the medial tibial malleolus. Blunt dissection is performed to expose the tibial nerve. The electrodes 16, 18 are inserted into the incision and are disposed subcutaneously in close proximity to the exposed section of the tibial nerve at approximately five centimeters cephalic to the medial tibial malleolus, and preferably at a ninety degree angle to each other. The placement of the electrodes 16, 18 is tested by turning on the transmitter 14 and bringing it into close proximity with the receiver head to cause the stimulating pulses to be generated and delivered to the tissue via the electrodes. If the electrodes are accurately placed, the patient's whole foot will typically curl or curve. Once proper placement of the electrodes is achieved, a loop suture may be made to secure the leads 26, 28 and/or the bases 30, 32 of the electrodes 16, 18 to the surrounding tissue to maintain proper placement. A subcutaneous pocket is made anterior to the incision at the base of the gastrocnemius muscle for the receiver head 20. The receiver head 20 is then inserted into the pocket. The incision is then closed and sutured over the implanted receiver 12.

Thereafter, the patient is allowed to heal post-surgically and is instructed concerning the proper use of the system. Prior to initiation of therapy, the physician or other caregiver uses a master programmer to program the microprocessor in the transmitter 14 with the proper treatment protocol. The patient is instructed to self-treat herself or himself using the system on a pre-determined basis. For treating urinary incontinence with the receiver implanted as illustrated in FIG. 14 for stimulating the tibial nerve, the patient may be instructed to self-treat as often as the patient deems necessary to control his/her incontinence, which may be several times per week, or possibly even daily. For example, a treatment protocol may involve treatments three times per week, with treatment durations for thirty minutes at pulse frequency of 20 Hz with pulse widths of 200 μs and amplitudes ranging from 0.1 mA to 10 mA.

The foregoing description is presented to enable one of ordinary skill in the art to make and use the invention and is provided in the context of a patent application and its requirements. Various modification to the preferred embodiment of the system and method of use and the generic principles and features described herein will be readily apparent to those of skill in the art. Thus, the present invention is not to be limited to the embodiments of the system and methods described above and illustrated in the drawing figures, but is to be accorded the widest scope consistent with the spirit and scope of the appended claims.

What is claimed is:

1. A method of treating urinary incontinence in a patient through neuromodulation of body tissue of the patient at a desired internal stimulation site, comprising:

implanting a receiver subcutaneously in the patient, the receiver comprising passive receiver circuitry, a dielectric, bio-compatible shell encapsulating the receiver circuit, a first elongated resiliently-insulated flexible helical electrically conductive wire lead extending from the shell, a first electrode disposed at a distal end of the first lead and electrically connected to the receiver circuitry through the first lead to function as an anode, a second elongated resiliently-insulated flexible helical electrically conductive wire lead extending from the shell, and a second electrode disposed at a distal end of the second lead and electrically connected to the receiver circuitry through the second lead to function as a cathode;

during the implanting step, positioning the first and second electrodes in proximity to a tibial nerve of the patient, approximately five centimeters cephalic to the medial tibial malleolus, by elongation of at least one of the first and second leads, and supplying a first pulsed alternating magnetic field to the receiver from a portable transmitter outside of the patient to test for accurate positioning of the first and second electrodes as indicated by a curl or curve of a foot of the patient; and supplying a second pulsed alternating magnetic field to the receiver from the portable transmitter outside of the patient, wherein the second pulsed alternating magnetic field comprises alternating magnetic field pulses have pulse frequency, pulse amplitude and pulse width characteristics corresponding to a predetermined treatment protocol for urinary incontinence; and wherein the first and second alternating magnetic field pulses inductively couple to the passive receiver circuitry to generate treatment current pulses therein in accordance with the treatment protocol, the treatment current pulses being supplied to the electrode through the lead for stimulating the tibial nerve.

2. The method of claim 1 further comprising:
adjusting the pulse frequency to a value between approximately four Hz and approximately forty Hz;
adjusting the pulse amplitude to a value between approximately 0.1 mA and approximately 20 mA; and
adjusting the pulse width in predefined increments.

3. A method of treating a patient for urinary incontinence by neuromodulation of a tibial nerve of the patient, said method comprising the steps of:
providing a portable transmitter, said transmitter being programmed with a treatment protocol for urinary incontinence and including circuitry to generate a pulsed alternating magnetic field in accordance with said treatment protocol;
implanting a receiver subcutaneously in said patient in relative proximity to said tibial nerve, said receiver having receiver circuitry that, when exposed to said pulsed alternating magnetic field, generates current pulses, said receiver circuitry being encapsulated in a dielectric, bio-compatible shell, and further wherein said receiver includes a first electrode disposed at a distal end of a first elongated, flexible lead and electrically connected to said receiver circuitry by the first lead to function as an anode, and a second electrode disposed at a distal end of a second elongated, flexible lead and electrically connected to said receiver circuitry by the second lead to function as a cathode, the first lead comprising a flexible, helical electrically conductive wire encapsulated within a dielectric, bio-compatible resilient casing, and the second lead comprising a flexible, helical electrically conductive wire encapsulated within a dielectric, bio-compatible resilient casing;
during the implanting step, positioning said first electrode and said second electrode in proximity to said tibial nerve by elongation of at least one of the first and second leads, and activating said transmitter to generate said pulsed alternating magnetic field to thereby cause said receiver to produce said current pulses for stimulating said tibial nerve, wherein accurate placement of the first and second electrodes is indicated by a curl or curve of a foot of the patient; and
activating said transmitter to generate said pulsed alternating magnetic field pursuant to said predetermined treatment protocol to thereby cause said receiver to produce said current pulses for stimulating said tibial nerve in proximity to said first and second electrodes.

4. The method of claim 3 wherein said treatment protocol includes a duration, further comprising selectively adjusting the duration of said treatment protocol at predetermined increments.

5. The method of claim 4 wherein said treatment protocol includes a pulse frequency, further comprising selectively adjusting the pulse frequency of said treatment protocol at predetermined increments.

6. The method of claim 5 wherein said treatment protocol includes a pulse amplitude, further comprising selectively adjusting the pulse amplitude of said treatment protocol in predetermined increments.

7. The method of claim 3 wherein said first electrode comprises two spaced, electrically independent buttons that function as anodes during said activating step, and wherein said second electrode comprises at least two spaced, electrically independent buttons that function as cathodes during said activating step.

8. The method of claim 7 wherein said first and second leads each includes at least two flexible, helical, electrically conductive wires encapsulated within said dielectric, bio-compatible casing with a distal end of each flexible, helical, electrically conductive wire of said first lead electrically connecting said receiver circuitry to each of said spaced, electrically independent buttons of the first electrode, and a distal end of each flexible, helical, electrically conductive wire of said second lead electrically connecting said receiver circuitry to each of said spaced, electrically independent buttons of the second electrode.

9. The method of claim 3 wherein said positioning step comprises positioning said first electrode and said second electrode in proximity to said patient's tibial nerve, approximately five centimeters cephalic to the medial tibial malleolus.

10. The method of claim 9 wherein said treatment protocol defines a treatment duration having a duration range of between approximately fifteen minutes and approximately 90 minutes, further comprising selectively adjusting the treatment duration to a value within the duration range.

11. The method of claim 10 wherein said treatment protocol defines a pulse frequency having a frequency range of between approximately four Hz and approximately forty Hz, further comprising selectively adjusting the pulse frequency to a value within the frequency range.

12. The method of claim 9 wherein said treatment protocol defines a pulse amplitude having an amplitude range of between approximately 0.1 mA and approximately 20 mA, further comprising selectively adjusting the pulse amplitude to a value within the amplitude range.

13. The method of claim 12 wherein said treatment protocol defines a pulse width that varies in predefined increments, further comprising selectively adjusting the pulse width to a value in accordance with the predefined increments.

* * * * *